United States Patent [19]
LeBoulch et al.

[11] Patent Number: 5,861,488
[45] Date of Patent: Jan. 19, 1999

[54] COMPOSITIONS AND METHODS FOR TREATING SICKLE CELL DISEASE

[75] Inventors: Philippe LeBoulch; Irving M. London, both of Cambridge, Mass.

[73] Assignee: Massachusetts Institute of Technology, Cambridge, Mass.

[21] Appl. No.: 935,648

[22] Filed: Sep. 23, 1997

Related U.S. Application Data

[63] Continuation of Ser. No. 308,795, Sep. 19, 1994, abandoned.

[51] Int. Cl.$^6$ .......................... C07K 14/805; C12P 21/06
[52] U.S. Cl. ......................................... 530/385; 435/69.1
[58] Field of Search ............................. 530/385; 435/69.1

[56] References Cited

U.S. PATENT DOCUMENTS 5,126,260   6/1992   Tuan et al. ............................ 435/240.2

FOREIGN PATENT DOCUMENTS

| WO 8902469 | 3/1989 | WIPO | ............................. C12N 15/00 |
| WO 91/19505 | 12/1991 | WIPO | ............................. A61K 35/14 |
| WO 94/29470 | 12/1994 | WIPO | ............................. A61K 48/00 |
| WO 95/00657 | 1/1995 | WIPO | ............................. A61K 35/14 |

OTHER PUBLICATIONS

Stamatoyannopoulos, George, M.D., Dr. Sci, et al., "Regulatory Elements of the Individual Globin Genes", *The Molecular Basis of Blood Diseases* (Second Edition), W.B. Saunders Company, pp. 116–120.

LeBoulch, Philippe, et al., "Mutagenesis of Retroviral Vectors Transducing Human β–Globin Gene and β–Globin Locus Control Region Derivatives Results in Stable Transmission of an Active Transcriptional Structure", *The EMBO Journal*, vol. 13, No. 13, (1994) pp. 3065–3076.

Kosche, Katherine A., "DNA Sequences Regulating Human β Globin Gene Expression", *Nucleic Acids Research*, vol. 13, No. 21 (1985), pp. 7781–7793.

Nagel, Ronald L., "Structural Bases of the Inhibitory Effects of Hemoglobin F and Hemoglobin A$_2$ on the Polymerization of Hemoglobin S", *Proc. Natl. Acad. Sci, USA*, vol. 76, No. 2 (Feb. 1979), pp. 670–672.

Lawn et al. 1980 Cell 21: 647–651.

Spritz et al 1980 Cell 21: 639–646.

Goodman et al 1983 Nature 303:546–548.

Nagai et al 1995 Blood 86(10):998A.

Curd, John G., et al., "Antibodies to an NH$_2$–terminal Fragment of β$^S$ Globin", *The Journal of Biological Chemistry*, vol. 251, No. 5 (Mar. 10, 1976) pp. 1290–1295.

Eastlake, Ann, et al., "The NH$_2$–terminal Region of the β Chain of Sickle Hemoglobin", *The Journal of Biological Chemistry*, vol. 251, No. 20 (Oct. 25, 1976) pp. 6426–6430.

Enver, Tariq, et al., "The Human β–globin Locus Activation Region Alters the Development Fate of a Human Fetal Globin Gene in Transgenic Mice", *Proc. Natl. Acad. Sci, USA*, vol. 86, (Sep. 1989) pp. 7033–7037.

McCune Steven L., et al., "Recombinant Human Hemoglobins Designed for Gene Therapy of Sickle Cell Disease" *Proc. Natl. Acad. Sci., USA*, vol. 91, (Oct. 1994), pp. 9852–9856.

Otieno, Samuel, et al., "Specific Antibodies to Hemoglobin A$_1$ (ant–Glu) and Hemoglobin S (anti–Val) in the Guinea Pig: Immunologic and Structural Correlations[1]", *The Journal of Immunology*, vol. 121, No. 6 (Dec. 1978), pp. 2458–2462.

Roth, Eugene F. Jr., et al., "Chemical Modification of Human Hemoglobin by Antisickling Concentrations of Nitrogen Mustard", *Blood*, vol. 58, No. 2 (Aug. 1981), pp. 300–308.

Takekoshi, Ken J., et al., "Retroviral Transfer of a Human β–globin/δglobin Hybrid Gene Linked to β Locus Control Region Hypersensitive Site 2 Aimed at the Gene Therapy of Sickle Cell Disease", *Proc. Natl. Acad. Sci., USA*, vol. 92, No. 7 (Mar. 1995) pp. 3014–3018.

*Primary Examiner*—Karen Cochrane Carlson
*Attorney, Agent, or Firm*—Thomas J. Engellenner; Jane E. Remillard

[57] ABSTRACT

Gene therapy methods and compositions for high level expression of anti-sickling globin proteins in erythroid cells for treating Sickle Cell disease are described.

11 Claims, 2 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 146 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:1:

```
Val His Leu Thr Pro Glu Glu Lys Ser Ala Val Thr Ala Leu Trp Gly
 1               5                  10                  15
Lys Val Asn Val Asp Glu Val Gly Gly Glu Ala Leu Gly Arg Leu Leu
            20                  25                  30
Val Val Tyr Pro Trp Thr Gln Arg Phe Phe Glu Ser Phe Gly Asp Leu
        35                  40                  45
Ser Thr Pro Asp Ala Val Met Gly Asn Pro Lys Val Lys Ala His Gly
    50                  55                  60
Lys Lys Val Leu Gly Ala Phe Ser Asp Gly Leu Ala His Leu Asp Asn
65                  70                  75                  80
Leu Lys Gly Thr Phe Ala Thr Leu Ser Glu Leu His Cys Asp Lys Leu
                85                  90                  95
His Val Asp Pro Glu Asn Phe Arg Leu Leu Gly Asn Val Leu Val Cys
            100                 105                 110
Val Leu Ala His His Phe Gly Lys Glu Phe Thr Pro Pro Val Gln Ala
        115                 120                 125
Ala Tyr Gln Lys Val Val Ala Gly Val Ala Asn Ala Leu Ala His Lys
    130                 135                 140
Tyr His
145
```

( 2 ) INFORMATION FOR SEQ ID NO:2:

( i ) SEQUENCE CHARACTERISTICS:
        ( A ) LENGTH: 146 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:2:

```
Val  His  Leu  Thr  Pro  Glu  Glu  Lys  Thr  Ala  Val  Asn  Ala  Leu  Trp  Gly
1              5                        10                       15

Lys  Val  Asn  Val  Asp  Ala  Val  Gly  Gly  Glu  Ala  Leu  Gly  Arg  Leu  Leu
               20                       25                       30

Val  Val  Tyr  Pro  Trp  Thr  Gln  Arg  Phe  Phe  Glu  Ser  Phe  Gly  Asp  Leu
          35                       40                       45

Ser  Ser  Pro  Asp  Ala  Val  Met  Gly  Asn  Pro  Lys  Val  Lys  Ala  His  Gly
     50                       55                       60

Lys  Lys  Val  Leu  Gly  Ala  Phe  Ser  Asp  Gly  Leu  Ala  His  Leu  Asp  Asn
65                       70                       75                       80

Leu  Lys  Gly  Thr  Phe  Ser  Gln  Leu  Ser  Glu  Leu  His  Cys  Asp  Lys  Leu
                    85                       90                       95

His  Val  Asp  Pro  Glu  Asn  Phe  Arg  Leu  Leu  Gly  Asn  Val  Leu  Val  Cys
               100                      105                      110

Val  Leu  Ala  Arg  Asn  Phe  Gly  Lys  Glu  Phe  Thr  Pro  Pro  Val  Gln  Ala
          115                      120                      125

Ala  Tyr  Gln  Lys  Val  Val  Ala  Gly  Val  Ala  Asn  Ala  Leu  Ala  His  Lys
     130                      135                      140

Tyr  His
145
```

(2) INFORMATION FOR SEQ ID NO:3:

(i) SEQUENCE CHARACTERISTICS:
   (A) LENGTH: 15 base pairs
   (B) TYPE: nucleic acid
   (C) STRANDEDNESS: single
   (D) TOPOLOGY: linear (ii) MOLECULE TYPE: cDNA (xi) SEQUENCE DESCRIPTION: SEQ ID NO:3:

AGCCTTCACC TTAGG                                                                           15

(2) INFORMATION FOR SEQ ID NO:4:

(i) SEQUENCE CHARACTERISTICS:
   (A) LENGTH: 15 base pairs
   (B) TYPE: nucleic acid
   (C) STRANDEDNESS: single
   (D) TOPOLOGY: linear (ii) MOLECULE TYPE: cDNA (xi) SEQUENCE DESCRIPTION: SEQ ID NO:4:

ACTTTGCCCC ACAGG                                                                           15

(2) INFORMATION FOR SEQ ID NO:5:

(i) SEQUENCE CHARACTERISTICS:
   (A) LENGTH: 15 base pairs
   (B) TYPE: nucleic acid
   (C) STRANDEDNESS: single
   (D) TOPOLOGY: linear (ii) MOLECULE TYPE: cDNA (xi) SEQUENCE DESCRIPTION: SEQ ID NO:5:

AGTCTTCTCC TCAGG                                                                           15

COMPOSITIONS AND METHODS FOR TREATING SICKLE CELL DISEASE

This application is a continuation of application Ser. No. 08/308,795 filed on Sep. 19, 1994 Entitled: "Compositions And Methods For Treating Sickle Cell Disease" abandoned.

GOVERNMENT SUPPORT

The work resulting in this invention was supported in part by a National Institute of Health Grant No. NIH-HL48374-01. The U.S. Government may therefore be entitled to certain rights in the invention.

BACKGROUND OF THE INVENTION

The sickling of erythrocytes in Sickle Cell Disease (SCD) is the result of a single amino-acid mutation, β6 [Glu to Val], which leads to the polymerization of hemoglobin S ($\alpha_2\beta^S_2$) in the tense (T), deoxygenated state. Long, multi-stranded fibers form within red blood cells (RBCs) of patients with SCD. The main fibers are made of 14 twisted strands associated by pairs (the Whisher-Lowe double-strand). The β6 Val mutation is required to initiate stable lateral contacts with another tetramer in the double-stranded unit. Only one β6 Val mutation per $\alpha_2\beta^S_2$ tetramer is involved in inter-tetramer contact, although many other amino-acid residues participate in lateral and axial contacts within the double-strand as well as between double-strands (Bunn, H. F. and Forget, B. G. (1986) *Hemoglobin: Molecular, Genetic and Clinical Aspects*, (W. B. Saunders Company, Philadelphia); Bunn, H. F. (1994) in *The Molecular Basis of Blood Diseases*, Second Edition, eds. Stamatoyannopoulos, G., Nienhuis, A., W., Majerus, P. W. and Varmus, H. (W. B. Saunders Company, Philadelphia), pp. 207–256; Dickerson, R. E. and Geis, I. (1983) *Hemoglobin: Structure, Function, Evolution, and Pathology* (The Benjamin/Cummings Publishing Company, Inc., Menlo Park, Calif.);. Schechter, A. N., Noguchi, C. T. and Rodgers, G. P. (1987) in *The Molecular Basis of Blood Diseases*, eds. Stamatoyannopoulos, G., Nienhuis, A., W., Leder, P. and Majerus, P. W. (W. B. Saunders Company, Philadelphia), pp. 179–218).

Mixing $\beta^S$ with the other normal human β-like globin chains ($\beta^X$), i.e. β-, δ- or or γ-, results in an equilibrium between symmetrical ($\alpha_2\beta^S_2$ and $\alpha_2\beta^X_2$) and hybrid ($\alpha_2\beta^S\beta^X$) tetramers, because interactions at α/β subunit interfaces within the same hemoglobin tetramer (packing and lateral contacts) are similar among β-like globin chains. Symmetrical tetramers that do not have the β6 Val mutation ($\alpha_2\beta^X_2$) are incorporated into the fibers very poorly. The $\alpha_2\beta^S\beta$ hybrid tetramers are capable of copolymerizing with hemoglobin S, because only one β6 Val residue per tetramer is required for inter-tetramer contact, and the other lateral and axial contacts are formed efficiently with the trans β subunit. In contrast, $\alpha_2\beta^S\gamma$ and $\alpha^2\beta^S\delta$ hybrid tetramers are poorly if at all incorporated, because trans δ- and γ- globin chains are unable to form important contacts within the S fiber even when the β6 Val residue of the $\beta^S$ subunit is aligned appropriately. This phenomenon is believed to explain why γ- and δ- globins are much stronger inhibitors of sickling than β-globin, in vitro. In addition, interaction of these hybrid tetramers with hemoglobin S without successful copolymerization is expected to delay the polymerization process in vivo, so that RBCs return to the lung to get reoxygenated before significant sickling has occurred (Benesch, R. E., Edalji, R., Benesch, R. and Kwong, S. (1980) *Proc. Natl. Acad. Sci. USA*, 77, 5130–5134; Cheetham, R. C., Huehns, E. R. and Rosemeyer, M. A. (1979) *J Mol. Biol.*, 129, 45–61; Sunshine, H. R., Hofrichter, J. and Eaton, W. A. (1979) *J. Mol. Biol.*, 133, 435–467; Bunn, H. F. and Forget, B. G. (1986) *Hemoglobin: Molecular, Genetic and Clinical Aspects*, (W. B. Saunders Company, Philadelphia); Bunn, H. F. (1994) in *The Molecular Basis of Blood Diseases*, Second Edition, eds. Stamatoyannopoulos, G., Nienhuis, A., W., Majerus, P. W. and Varmus, H. (W. B. Saunders Company, Philadelphia), pp. 207–256; Dickerson, R. E. and Geis, I. (1983) *Hemoglobin: Structure, Function, Evolution, and Pathology* (The Benjamin/Cummings Publishing Company, Inc., Menlo Park, Calif.) Schechter, A. N., Noguchi, C. T. and Rodgers, G. P. (1987) in *The Molecular Basis of Blood Diseases*, eds. Stamatoyannopoulos, G., Nienhuis, A., W., Leder, P. and Majerus, P. W. (W. B. Saunders Company, Philadelphia), pp. 179–218).

The actual inhibitory effect of δ chains has not yet been assessed in vivo, because the δ-globin gene is always expressed at very low levels in human RBCs. In contrast, there is a strong correlation between high expression levels of γ chains and a lower propensity for sickling in vivo, as observed for instance in certain forms of SCD associated with hereditary persistence of fetal hemoglobin (HPFH) (Bunn, H. F. and Forget, B. G. (1986) *Hemoglobin: Molecular, Genetic and Clinical Aspects*, (W. B. Saunders Company, Philadelphia); Bunn, H. F. (1994) in *The Molecular Basis of Blood Diseases*, Second Edition, eds. Stamatoyannopoulos, G., Nienhuis, A., W., Majerus, P. W. and Varmus, H. (W. B. Saunders Company, Philadelphia), pp. 207–256; Dickerson, R. E. and Geis, I. (1983) *Hemoglobin: Structure, Function, Evolution, and Pathology* (The Benjamin/Cummings Publishing Company, Inc., Menlo Park, Calif.);. Schechter, A. N., Noguchi, C. T. and Rodgers, G. P. (1987) in *The Molecular Basis of Blood Diseases*, eds. Stamatoyannopoulos, G., Nienhuis, A., W., Leder, P. and Majerus, P. W. (W. B. Saunders Company, Philadelphia), pp. 179–218).

In addition, drugs known to derepress partially γ-globin gene expression, such as hydroxyurea and butyrate derivatives, are clearly beneficial to SCD patients. However, these approaches do not represent a definitive cure and have raised legitimate concerns regarding their potential long-term consequences, which include teratogenic and oncogenic effects for hydroxyurea and neurotoxicity and multiorgan damage for butyrate. In addition, drug induced γ-globin expression might be largely restricted to F cells, so that non-F cells may still sickle in SCD (Stamatoyannopoulos, G. and Nienhuis, A., W., (1994) in *The Molecular Basis of Blood Diseases*, Second Edition, eds. Stamatoyannopoulos, G., Nienhuis, A. W., Majerus, P. W. and Varmus, H. (W. B. Saunders Company, Philadelphia), pp. 107–155).

New therapies for treating a subject afflicted with sickle cell disease are needed.

SUMMARY OF THE INVENTION

In general, the invention relates to gene therapy methods and compositions for treating a subject afflicted with Sickle Cell disease. High level expression of anti-sickling globin proteins as described herein can effectively interfere with the polymerization of hemoglobin S and thereby reduce or eliminate the symptoms associated with Sickle Cell disease.

In one aspect, the invention features new anti-sickling globin proteins comprising conformationally correct β globin in which at least one amino acid residue has been substituted with a corresponding residue (an anti-sickling residue) from a δ- or γ- globin. In a preferred embodiment, the β, δ and γ globins are human. In another preferred embodiment, the anti-sickling residue is selected from the group consisting of: 9 Thr, 12 Asn, 22 Ala, 50 Ser, 80 Asp, 86 Ser, 87 Gln, 116 Arg, 117 Asn, 125 Gln, 126 Met. In a particularly preferred embodiment, the anti-sickling β-globin protein comprises the 146 amino acids of β-globin with the following substitutions: 9 Thr, 12 Asn, 22 Ala, 50 Ser, 86 Ser, 87 Gln, 116 Arg and 117 Asn.

In another aspect, the invention relates to genetic material encoding anti-sickling β-globin proteins. In one embodiment, the genetic material is deoxyribonucleic acid (DNA). In another embodiment, the genetic material is ribonucleic acid (RNA).

In a further aspect, the invention relates to gene constructs comprising genetic material encoding anti-sickling β-globin proteins and an appropriate transcriptional control element. In a first embodiment, the genetic material encoding an anti-sickling β-globin protein is DNA and the transcriptional control element is a promoter recognized by a DNA polymerase. In a preferred embodiment, the DNA polymerase is erythroid specific. In a particularly preferred embodiment, the promoter is the β-globin promoter or HPFH promoter. In a second embodiment, the genetic material encoding an anti-sickling β-globin protein is RNA and the transcriptional control element is a promoter recognized by an RNA polymerase. A gene construct encoding an anti-sickling β-globin protein can additionally comprise an enhancer sequence. In a preferred embodiment, the enhancer sequence is the DNAse I hypersensitive site 2 of the human β Locus Control Region. A gene construct encoding an anti-sickling β-globin protein can also encode a selectable marker, which is useful in ex vivo gene therapy procedures for selecting erythroid cells containing the anti-sickling encoding construct.

In yet another aspect, the invention relates to vectors comprising elements for introducing and stably maintaining a gene construct encoding an anti-sickling β-globin protein into a erythroid cell and a gene construct encoding an anti-sickling β-globin protein. Preferred gene therapy vectors are selected from the group consisting of: retrovirus, adenovirus, adeno-associated virus, naked plasmid, lipid delivery of plasmid (including via liposomes), receptor mediated delivery of plasmid, alone, or in conjunction with transferring DNA-polylysine complexes linked to adenovirus capsids. A particularly preferred vector comprises retroviral elements.

In still another aspect, the invention relates to gene therapy methods for treating a subject with sickle cell disease. In one embodiment, erythroid cells from a subject or from a donor are obtained and are contacted with a suitable vector encoding an anti-sickling β-globin protein in vitro. Erythroid cells expressing the anti-sickling β-globin proteins are then selected (e.g. based on expression of an anti-sickling β-globin protein or a selectable marker that has been included in the gene construct) and infused into the subject (e.g. via graft or transplantation). In another embodiment, a vector encoding an anti-sickling β-globin protein is admininistered directly to a subject in vivo.

Other features and advantages will be readily apparent from the following detailed description and claims.

DETAILED DESCRIPTION OF THE INVENTION

Figure 1:
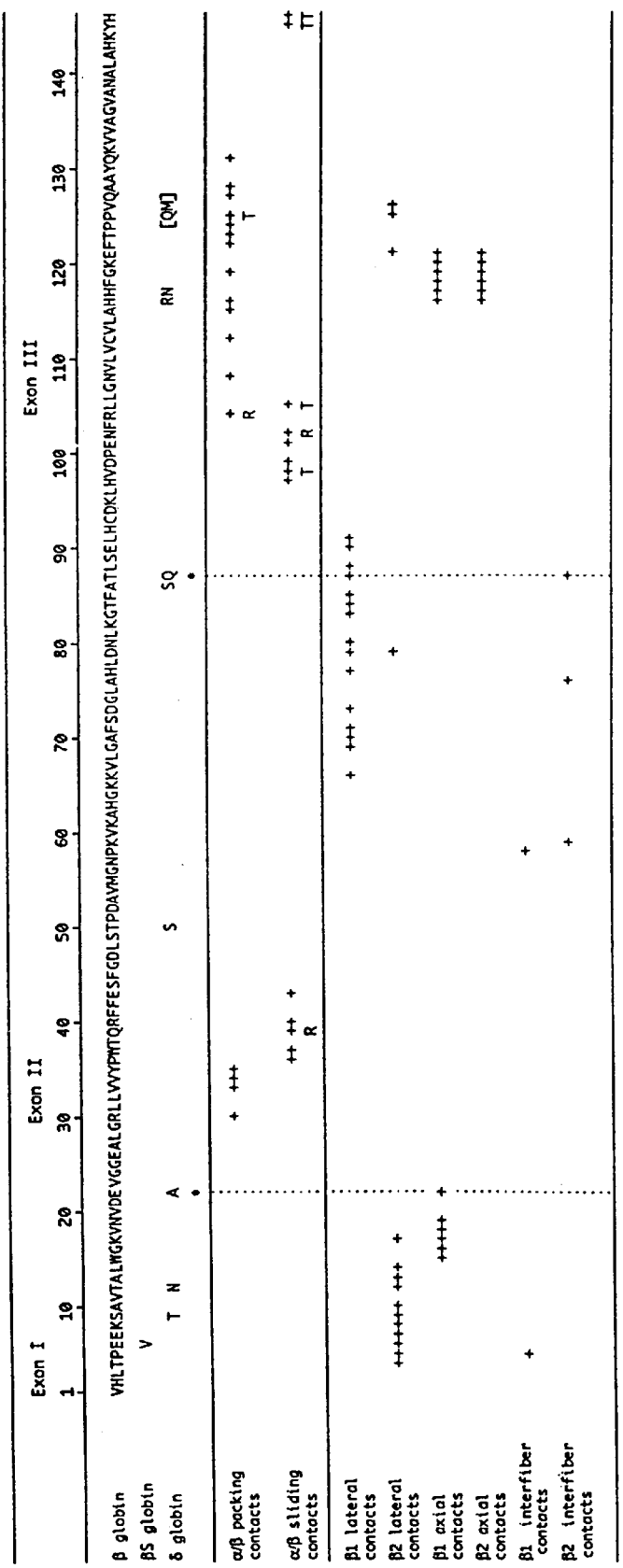
FIG. 1 is a graphic representation of the amino-acid sequence alignment of human β-, $\beta^S$- and δ-globins. The two amino-acids residues δ 125Gln and δ 126Met that were not incorporated in the [β/δ-SCl1/HS2] retroviral vector are indicated within brackets [QM]. Anti-sickling residues δ 87Gln and δ 22Ala are indicated by an asterisk and a vertical, dashed line. The α/β packing and sliding contacts within the globin tetramer are indicated by "+"; contacts present only in the relaxed (R) "oxy" or tense (T) "deoxy" states are indicated by R or T, respectively; the $\beta_1$ and $\beta_2$, lateral and axial contacts within the Wisher-Lowe double-strands of the Hb S polymer are indicated by a "+".

The instant invention is based on the finding that retroviral transfer of genetic material encoding anti-sickling β-globin protein into erythroid cells results in high and erythroid specific expression of an anti-sickling β-globin protein. Based on this finding, the invention features anti-sickling β-globin proteins; methods for making the proteins; constructs and vectors useful in making the proteins; and methods for delivering the constructs to erythroid cells for treating sickle cell disease.

Anti-sickling β-globin Proteins

The γ- and δ-globin chains have been found to be more potent inhibitors of sickling than β chains in vitro (Benesch, R. E., Edalji, R., Benesch, R. and Kwong, S. (1980) Proc. Natl. Acad. Sci. USA, 77, 5130–5134; Cheetham, R. C., Huehns, E. R. and Rosemeyer, M. A. (1979) J. Mol. Biol., 129, 45–61; Sunshine, H. R., Hofrichter, J. and Eaton, W. A. (1979) J. Mol. Biol., 133, 435–467). However, both γ-globin and δ-globin genes are expressed at very low levels in normal adult RBCs.

However, as shown herein, high expression levels of anti-sickling β-globin chain proteins with anti-sickling properties can be obtained from expressions of constructs that maintain the general structure of the β-globin gene and its cis-acting elements, while substituting nucleotides encoding "anti-sickling" amino-acid residues from either γ or δ chains for corresponding codons in the β-globin gene.

Nagel and colleagues have attempted to assign the anti-sickling effect of δ and γ chains to specific amino-acid residues (Nagel, R. L., Bookchin, R. M., Johnson, J., Labie, D., Wajcman, H., Isaac-Sodeye, W. A., Honig, G. R., Schiliro, G., Crookston, J. H. and Matsutomo, K. (1979) Proc. Natl. Acad. Sci., USA, 76, 670–672). Because of the few differences between β and δ chains (10 of their 146 residues) and the existence of natural β/δ hybrid chains, the Lepore globins, Nagel and colleagues have succeeded in assigning most of the in vitro anti-sickling properties of δ chains to residues δ 22Ala and δ 87Gln, with possible additional contribution of δ 12Asn (Nagel, R. L., Bookchin, R. M., Johnson, J., Labie, D., Wajcman, H., Isaac-Sodeye, W. A., Honig, G. R., Schiliro, G., Crookston, J. H. and Matsutomo, K. (1979) Proc. Natl. Acad. Sci., USA, 76, 670–672). Interestingly, β87 and β22 are believed to occupy critical positions for contacts between tetramers in the HbS fiber, both within the Whisher-Lowe double-strand (for β87 and β22) (Bunn, H. F. and Forget, B. G. (1986) Hemoglobin: Molecular, Genetic and Clinical Aspects, (W. B. Saunders Company, Philadelphia); Bunn, H. F. (1994) in The Molecular Basis of Blood Diseases, Second Edition, eds. Stamatoyannopoulos, G., Nienhuis, A., W., Majerus, P. W. and Varmus, H. (W. B. Saunders Company, Philadelphia), pp. 207–256; Dickerson, R. E. and Geis, I. (1983) Hemoglobin: Structure, Function, Evolution, and Pathology (The Benjamin/Cummings Publishing Company, Inc., Menlo Park, Calif.); Schechter, A. N., Noguchi, C. T. and Rodgers, G. P. (1987) in The Molecular Basis of Blood Diseases, eds. Stamatoyannopoulos, G., Nienhuis, A. W., Leder, P. and Majerus, P. W. (W. B. Saunders Company, Philadelphia), pp. 179–218) and for inter-strand packing (β87) (Cretegny, I. and Edelstein, S. J. (1993) J. Mol. Biol., 230, 733–738) (FIG. 1).

γ and β chains have differing amino acids in 39 out of the total 146 residues. Interestingly, the same amino-acid change exists at position 87 in the γ- and δ-globins as compared to β-globin (δ 87Gln and γ 87Gln versus β 87Thr), and this substitution also appears critical for the anti-sickling activity of γ-globin (Nagel, R. L., Bookchin, R. M., Johnson, J., Labie, D., Wajcman, H., Isaac-Sodeye, W. A., Honig, G. R., Schiliro, G., Crookston, J. H. and Matsutomo, K. (1979) Proc. Natl. Acad. Sci., USA, 76, 670–672). However, other residues cooperate with γ 87Gln to provide the maximum effect, including γ 80Asp and other unassigned residues (Nagel, R. L., Bookchin, R. M., Johnson, J., Labie, D., Wajcman, H., Isaac-Sodeye, W. A., Honig, G. R., Schiliro, G., Crookston, J. H. and Matsutomo, K. (1979) Proc. Natl. Acad. Sci., USA, 76, 670–672).

FIG. 1 is a graphic representation of the amino-acid sequence alignment of human β-, β$^S$- and δ-globins. Based on the known amino acid sequence of β-globin and δ-globin, anti-sickling globin proteins can be designed.

Example 1 describes the design of a δ-globin/β-globin hybrid gene, β/δ-SCl1 which encodes an anti-sickling β-globin protein comprising the 146 amino acids of β-globin with the following substitutions: 9 Thr, 12 Asn, 22 Ala, 50 Ser, 86 Ser, 87 Gln, 116 Arg and 117 Asn. High expression levels of this construct were achieved in adult erythroid cells. Evaluation of expression level as described herein can provide a preliminary assay for identifying other constructs encoding anti-sickling β-globin proteins. Further evaluation of candidate constructs showing high expression, can be carried out for example in transgenic animal models of Sickle Cell disease. Expression of constructs encoding effective anti-sickling β-globin proteins will minimize or ameliorate the sickle cell condition.

Gene Constructs

Genetic material (i.e. DNA or RNA) encoding anti-sickling β-globin proteins can be synthesized using known techniques. Alternatively, the material can be isolated from natural sources and be further manipulated (e.g. via site-specific mutagenesis). Gene constructs comprising the genetic material and an appropriate transcriptional control element can then be generated. Where the genetic material is DNA, an appropriate transcriptional control element is a promoter recognized by a DNA polymerase. For safety reasons, the DNA polymerase is preferably erythroid specific (i.e. is only expressed in erythroid cells). Known erythroid specific promoters include the β-globin promoter or HPFH promoter. If the genetic material encoding an anti-sickling β-globin protein is RNA an appropriate promoter must be recognized by an RNA polymerase.

In addition to a promoter, a gene construct encoding an anti-sickling β-globin protein can additionally comprise and enhancer sequence. In a preferred embodiment, the enhancer sequence is the DNAse I hypersensitive site 2 of the human β Locus Control Region. Another enhancer that can be included in a construct in addition to or in place of the DNAse I hypersensitive site 2 of the human β Locus Control Region, is the second intron of the β-globin gene (BIVS2).

A gene construct encoding an anti-sickling β-globin protein can also encode a selectable marker (e.g. neomycin, methotrexate) which is useful in ex vivo gene therapy procedures for selecting erythroid cells containing the anti-sickling encoding construct.

Vectors

A preparation of an anti-sickling β-globin gene can be incorporated in a suitable vector for delivering the gene to appropriate cells ex vivo or in vivo for treating a subject suspected or known to have sickle cell disease (SCD). Appropriate gene therapy vectors preferably are capable of infecting erythroid cells (e.g. stem cells and more differentiated cells of the red blood cell lineage (such as BFUs (burst forming unit), CFUs (colony forming unit), nucleated red blood cells and mature red blood cells). For use in clinical treatment, appropriate vectors must also be appropriately maintained in erythroid cells and be safe. Appropriate vectors for use in the instant invention include: retrovirus; adenovirus (Berkner, K. L. (1988) BioTechniques 6:616); adeno-associated virus (Muzyczka, N. (1992) in Current Topics in Microbiology and Immunology 158:97); naked plasmid (Wolff, J. et al. (1989) Science 247:1465); lipid delivery of plasmid (including via liposomes) (Felgner, P. and Ringold, G. M. (1989) Nature 337:387); receptor mediated delivery of plasmid, alone (Wu, G. and Wu, C. H. (1988) J. Biol. Chem. 263:14621) or in conjunction with transferring DNA-polylysine complexes linked to adenovirus capsids (Curiel, D. T. et al. (1991) Proc. Natl. Acad. Sci. USA 88:8850); or any other vector that can infect and be maintained in erythroid cells and does not adversely effect the host.

Preferred gene therapy vectors for delivery of genetic material encoding anti-sickling β-globin proteins are defective retroviruses, which are the best characterized system to date and so far the only one approved for use in human gene therapy (Miller, A. D. (1990) Blood 76:271). Several requirements need to be met for successful gene therapy using retrovirus mediated gene transfer: (i) stable proviral transmission; (ii) high titer and/or efficient selection of transduced erythroid cells for sustained reconstitution of engrafted individuals with infected bone marrow cells; (iii) high, position-independent and erythroid specific β-globin expression; (iv) safety.

Although the design of retroviral vectors transducing β-globin gene and β-LCR derivatives has been faced with important technical difficulties (Novak, U., Harris, E. A. S., Forrester, W., Groudine, M. and Gelinas, R. (1990) Proc. Natl. Acad. Sci., USA, 87, 3386–3390; Chang, J. C., Liu, D. and Kan, Y. W. (1992) Proc. Natl. Acad. Sci. USA, 89, 3107–3110; Plavec, I., Papayannopoulou, T., Maury, C. and Meyer, F. (1993) Blood, 81, 1384–1392), [β-globin/LCR] retroviral vectors capable of stable proviral transmission and high erythroid-specific β-globin mRNA expression have recently been obtained (Leboulch, P., Huang, G. M. S., Humphries, R. K., Oh, Y. H., Eaves, C. J., Tuan, D. Y. H. and London, I. M. (1994) EMBO J., 13 (1994)).

Figure 2:
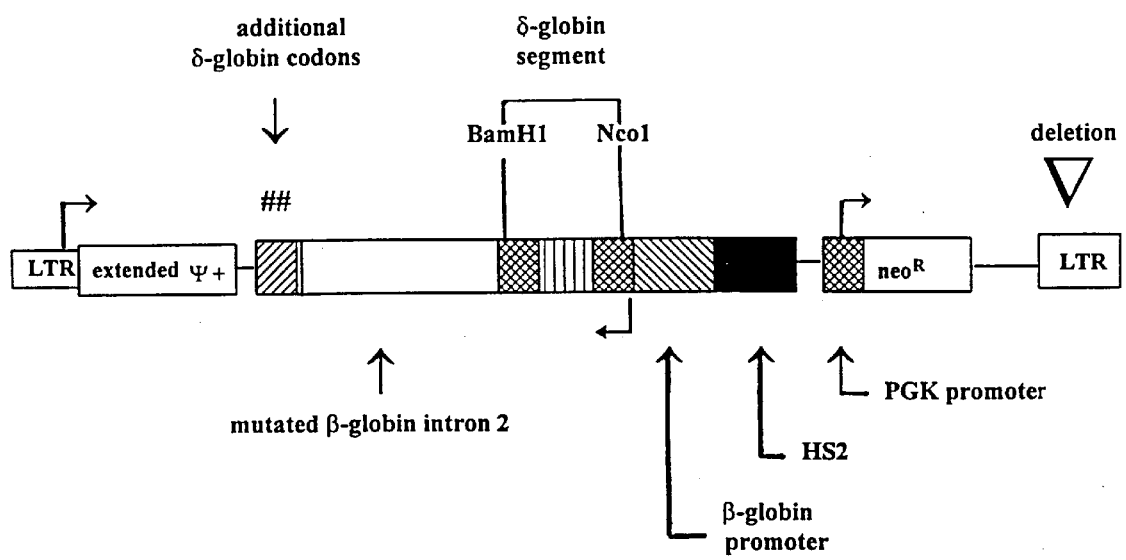
FIG. 2 shows a schematic representation of the structure of the [β/δ-globin/HS2] retroviral vector, p#147.

FIG. 2 shows a schematic representation of the structure of the [β/δ-globin/HS2] retroviral vector, p#147. The β/δSCll retroviral vector comprises from 5'0 to 3': (1) the Moloney Murine Sarcoma Virus (MoMSV) long terminal repeat (LTR) followed by the hybrid extended packaging signal of LXSN, (2) a mutated human β-globin gene in reverse genomic orientation driven by the human β-globin promoter, (3) the HS2 site from the human β-LCR in reverse genomic orientation, (4) the murine PGK-1 promoter in direct genomic orientation, (5) the Neo$^R$ gene, (6) the Moloney Murine Leukemia Virus (MoMLV) polypurine track (PPT), and (7) a modified MoMLV LTR. The β-globin gene was inserted in reverse orientation with respect to the direction of transcription of the provirus to prevent splicing of the β-globin introns on the viral genomic RNA prior to reverse transcription. For safety and for the prevention of a possible antisense effect due to the reverse orientation of the transduced β-globin promoter, a self-inactivating LXSN vector was created by making a 176 bp [Pvu2-Xba1] deletion in the 3' LTR (Leboulch, P et. al., (1994)). The 5' border of the human β-globin promoter is the SnaB1 site 266 bp upstream of the b-globin mRNA cap site. The 30 bp downstream of the gene were retained for cleavage/polyadentylation. The HS2 element was a 374 bp [Hind3-Xbal] HS2 fragment from the human b-LCR (23, 24, 25, 26).

The human β-globin gene in [β globin/LCR/PGK]$^{mut}$ retroviral vector also contains deletions and mutations that increase stability of proviral transmission and viral titers while being neutral for β-globin gene expression (Leboulch, P. et. al., (1994) The EMBO Journal 13:3065–3076). These modifications include: (1) a 372 bp deletion in β IVS2 between two Rsal sites located at +580 and +952 downstream from the human β-globin cap site, and (2) point mutations of complementary/reverse (C/R) polyadenylation signals (Poly A) and C/R splice sites (SS).

The [β/δ SCII/HS2] retroviral vector p#147 was constructed as follows. A 430 bp [Ncol-BamHl] fragment of the human δ-globin gene, that contains the segment of the δ-globin gene described above, was used to replace the corresponding fragment of the human β-globin gene in the [β-globin/LCR/PGK]$^{mut}$ retroviral vector (FIG. 2). This substitution introduces 6 of the 10 codons specific for the δ-globin gene, including all the positions that encode "anti-sickling" residues identified by Nagel and colleagues. In exon III, two additional changes, [β 116His to d 116Arg] and [β 117His to d 117Asn], were introduced by recombinant polymerase chain reaction (PCR) with mutated primers used previously for deleting part of βIVS2 in the β-globin/LCR/PGK]$^{mut}$ retroviral vector (15) (FIG. 2).

C/R SS and Poly A can lead to rearrangements of the transmitted proviral structures in [β-globin/LCR] retroviral vectors (Leboulch, P. et. al., (1994) The EMBO Journal 13:3065–3076)), the DNA sequence of the aforementioned [Ncol-BamHl] fragment of the human d-globin gene for the presence of such deleterious features, using the same methodology previously employed (Leboulch, P. et. al., (1994) The EMBO Journal 13:3065–3076). No [AATAAA] signals were found. In contrast, several potentially dangerous C/R SS were identified. These include three 3'SS, [agCCTTCaCCTTAGG](SEQ ID NO:3) [aCTTTgCCCCACAGG](SEQ ID NO:4) and [agTCTTCTCCTCAGG](SEQ ID NO:5), 111 bp, 372 bp and 398 bp downstream from the Ncol site in C/R orientation, respectively. The two last 3'SS also possess well conserved branchpoint signals at an appropriate distance upstream. A well conserved 5'SS is also present, [CAG GTGAGC], 63 bp downstream from the Ncol site in C/R orientation. Since proviral transmission of a non-mutated [β-globin/HS2/PGK] retroviral vector was stable when no additional LCR derivatives were incorporated in the vector (15), whether retroviral vector p#147 was stable was determined.

To study proviral transmission and to measure viral titers, MEL and NIH 3T3 cells were infected by exposure to viral supernatants from pooled Ψcrip stable producer cells or from transiently transfected BOSC23 cells. Infected cells were subsequently selected with G418. Proviral transmission was analyzed by Southern blot using a Neo$^R$-specific probe after restriction digestion of genomic DNA with Sacl, which cuts only once in each LTR. Corresponding digested plasmids were used as size controls. Results from the Southern blot analysis indicate that proviral transmission was stable, without detected rearrangements. Viral titers, obtained from transiently transfected BOSC23 cells, were 2×10$^4$ cfu/ml for both the retroviral vector p#147 and [b-globin/HS2/PGK]$^{mut}$, indicating that these vectors had very similar transmission properties. In light of previous results with [β-globin/HS2/PGK]$^{mut}$ producers (Leboulch, P. et. al., (1994) The EMBO Journal 13:3065–3076), the best independent p#147 Ψcre producers would be expected to reach titers above 10$^5$ cfu/ml. No helper virus was detected using a β-galactosidase mobilization assay in any of the viral producers.

β/δ-SCIl mRNA expression levels in DMSO-induced MEL cells, which mimic adult erythroid differentiation was measured. MEL cells were infected with supernatants from amphotropic producers under experimental conditions that provided up to one integrated provirus per cell, and were subsequently selected with G418. Pools of at least one hundred infected and selected MEL cell clones were analyzed, either without induction or following exposure to DMSO for five days to induce terminal erythroid differentiation. Human and murine β-globin mRNA levels were measured by RNA protection assay using probes specific for DNA sequences in either murine $β_{maj}$- or human δ-globin mRNAs, as described in Example 1. The results demonstrate that human β/δ-SCIl mRNA was properly initiated and spliced in infected MEL cells. The mRNA ratios were calculated on a per gene basis, with appropriate corrections. In infected (one provirus per cell), G418 selected, and DMSO-induced MEL cells, expression levels of β/δ-SCIl mRNA using the p#147 virus reached 85% of murine $β_{maj}$-globin mRNA, corrected on a per-gene basis as described in the examples.

Gene Therapy

The high expression levels of vectors encoding anti-sickling β-globin proteins, make them useful for gene therapies for preventing or reducing or eliminating the symptoms of Sickle Cell disease. Gene therapies can be performed by infecting erythroid cells with a vector encoding an anti-sickling β-globin protein as described above. In general, ex vivo gene therapy of Sickle Cell disease is performed on erythroid cells obtained from a subject's (e.g. human's or animal's) bone marrow, which had been removed (for example, by aspiration under sterile conditions). The bone marrow cells are then incubated with the vector. The treated bone marrow cells are then reinfused into the patient (e.g. via transplantation or grafting). The procedure can be repeated several times in order to increase the total number of marrow erythroid cells expressing the anti-sickling β globin protein. Alternatively, the erythroid cells can be obtained from a donor (i.e. a compatible source other than the recipient), modified and delivered to the recipient, again by transplanting or grafting.

Alternatively, an "effective amount" of vector encoding an anti-sickling β globin and a pharmaceutically acceptable carrier (e.g. saline) can be administered to a Sickle Cell disease subject directly. As used herein, an "effective amount" is an amount sufficient to reduce or eliminate the symptoms associated with Sickle Cell disease. The effective amount can be determined by one of skill in the art using no more than routine experimentation and may take into account such factors as the type and severity of symptoms being treated, the weight and/or age of the subject, the previous medical history of the subject and the selected route of administration. Exemplary modes of administration of an anti-sickling β globin gene therapy vector includes subcutaneously, intravenously, intraperitoneally, intramuscularly, parenterally, submucosally, orally, transdermally or other appropriate manner. If necessitatted by a particular mode of administration, an anti-sickling β globin gene therapy vector can be encapsulated within a material that protects it from enzymatic degradation.

The present invention is further illustrated by the following examples which should not be construed as limiting in any way. The contents of all cited references (including literature references, issued patents, published patent applications, and co-pending patent applications) cited throughout this application are hereby expressly incorporated by reference.

EXAMPLE 1

Retroviral Transfer of Human δ-globin/β-globin Hybrid Gene

DNA Construction

The retroviral vector [β-globin/LCR/PGK]$^{mut}$ has been described (Leboulch, P., Huang, G. M. S., Humphries, R. K, Oh, Y. H., Eaves, C. J., Tuan, D. Y. H. and London, I. M. (1994) EMBO J., 13, (1994)). It contains elements from the vector LXSN (Miller, A. D. and Rosman, G. J. (1989) BioTechniques, 7, 980–990) provided by Dusty Miller (Fred Hutchinson Cancer Research Center, Seattle), and human b-LCR and β-globin gene sequences provided by Tom Maniatis (Harvard University, Cambridge) and Oliver Smithies (University of North Carolina, Chapel Hill). The δ-globin gene was provided by Oliver Smithies. The murine b$_{maj}$-globin gene was provided by Deborah Galson (Harvard Medical School, Boston). The murine phosphoglycerate kinase (PGK) -1 promoter/Neomycin phosphotransferase (Neo$^R$) cassette was provided by Rudolf Jaenisch (Whitehead Institute and MIT, Cambridge). All constructions were made using standard techniques (Sambrook, J., Fritsch, E. F. and Maniatis, T. (1989) Molecular cloning: a laboratory manual—2nd ed. Cold Spring Harbor Laboratory Press, Cold Spring Harbor, N.Y., USA). Oligonucleotides were synthesized at the MIT Biopolymer Laboratory.

Production of Recombinant Retroviruses

The packaging cell lines Ψcre and Ψcrip, provided by Richard Mulligan (Whitehead Institute and MIT, Cambridge), were grown as described (Danos, O. and Mulligan, R. C. (1988) Proc. Natl. Acad. Sci. USA, 85, 6460–6464). The packaging cell line BOSC23, provided by David Pear and David Baltimore (Rockefeller University, New York), was grown as described (Paer, W. S., Nolan, G. P., Scott, M. L. and Baltimore, D. (1993) Proc. Natl. Acad. Sci., USA, 90, 8392–8396). Plasmid DNAs used for transfection were prepared by the Qiagen procedure (Qiagen, Inc). Since self-inactivating vectors were used, Plasmid DNAs were directly transfected into packaging cells using a calcium phosphate procedure (5prime:3prime, Inc), after linearization of the Plasmids outside the proviral structure (Ndel site) for Ycre and Ycrip cells or without linearization for BOSC23 cells. Viral supernatants were harvested two days after transient transfection of BOSC23 cells, as described (Danos, O. and Mulligan, R. C. (1988) Proc. Natl. Acad. Sci. USA, 85, 6460–6464). Pools of Ycre and Ycrip producer cells were isolated and expanded following G418 selection (500 mg/ml active) (Gibco). Viruses were prepared by filtration of supernatants through 0.45 mm Millipore filters as described (Leboulch, P., Huang, G. M. S., Humphries, R. K., Oh, Y. H., Eaves, C. J., Tuan, D. Y. H. and London, I. M. (1994) EMBO J., 13, (1994); Danos, O. and Mulligan, R. C. (1988) Proc. Natl. Acad. Sci. USA, 85, 6460–6464). Detection of helper viruses was performed by a b-galactosidase mobilization assay as described (Danos, O. and Mulligan, R. C. (1988) Proc. Natl. Acad. Sci. USA, 85, 6460–6464).

Proviral Transmission and Virus Titration

NIH 3T3 cells were infected with various dilutions of filtered viral supernatants in the presence of 8 mg/ml Polybrene (Sigma), as described ((Leboulch, P., Huang, G. M. S., Humphries, R. K., Oh, Y. H., Eaves, C. J., Tuan, D. Y. H. and London, I. M. (1994) EMBO J., 13, (1994); Danos, O. and Mulligan, R. C. (1988) Proc. Natl. Acad. Sci. USA, 85, 6460–6464). Cells were subsequently transferred to in medium containing 500 mg/ml active G418. Resistant colonies were counted, and titers were estimated by standard calculations previously described (Leboulch, P., Huang, G. M. S., Humphries, R. K., Oh, Y. H., Eaves, C. J., Tuan, D. Y. H. and London, I. M. (1994) EMBO J., 13, (1994); Danos, O and Mulligan, R. C. (1988) Proc. Natl. Acad. Sci. USA, 85, 6460–6464). Proviral transmission was tested by Southern blot analysis of SacI-digested DNA from infected cells using a Neo$^R$-specific probe and appropriate plasmid controls.

Infection of MEL Cells and RNA Protection Assays

Semi-adherent (APRT-) MEL cells were grown at 37° C. with 5% $CO_2$/95% air in DMEM supplemented with 12% horse serum, 4.5 mg/ml glucose, 2 mM glutamine, 100 IU/ml penicillin and 100 mg/ml streptomycin. Infections of cells were performed with 3 ml of filtered supernatant from viral producers in the presence of 8 mg/ml Polybrene as described above. Infected cells were subsequently grown in medium containing 500 mg/ml active G418. Pools of resistant colonies were isolated and expanded. MEL cells were induced for 5 days at 37° C. with 5% $CO_2$/95% air in DMEM supplemented with 15% fetal calf serum, 4.5 mg/ml glucose, 2 mM glutamine, 100 IU/ml penicillin, 100 mg/ml streptomycin and 2% dimethylsulfoxide (DMSO) (Sigma). Total RNA was extracted by the RNAzol B method (Biotecx Laboratories, Inc). Quantitative RNA protection assays were performed with uniformly labeled RNA probes in vitro transcribed using SP6 or T7 polymerase (Gibco) in the presence of [a-$^{32}$P] UTP (Amersham). RNA protection assays were performed as described (Leboulch, P., Huang, G. M. S., Humphries, R. K., Oh, Y. H., Eaves, C. J., Tuan, D. Y. H. and London, I. M. (1994) EMBO J., 13, (1994); Sambrook, J., Fritsch, E. F. and Maniatis, T. (1989) Molecular cloning: a laboratory manual-2nd ed. Cold Spring Harbor Laboratory Press, Cold Spring Harbor, N.Y., USA), with the following conditions: 10 mg of total RNA, >5×10$^5$ cpm of each probe in separate reactions, hybridization at 52° C. for 16 hours in [40 mM PIPES, pH6.4, 400 mM NaCl, 1 mM EDTA, 80% formamide], followed by digestion with 20 mg/ml RNase A (Sigma) and 2 mg/ml RNase T1 (Sigma) for 30 min at room temperature. RNA protection samples containing murine β-globin and human δ-globin probes were combined at 1:2 ratio prior to loading onto a 6% polyacrylamide gel. A human δ-globin-specific probe was constructed by sub-cloning a T7 promoter in reverse genomic orientation at the BamHl site of d exon II, and linearizing the template prior to in vitro transcription at the Ncol site that overlaps the initiator "ATG" in d exon I. The specific protected fragment is 210 bp long and corresponds to most of d exon II up to the exonic BamHl site. A murine-specific probe, previously described (Leboulch, P., Huang, G. M. S., Humphries, R. K., Oh, Y. H., Eaves, C. J., Tuan, D. Y. H. and London, I. M. (1994) EMBO J., 13, (1994)), was used as an internal control for murine endogenous mRNA expression. This probe protects a 145 bp fragment corresponding to exon I of the murine b$_{maj}$-globin mRNA. Because of extensive homology between β$_{maj}$- and β$_{min}$-globin mRNAs and the conditions of our RNA protection assay, the murine specific probe also protects a 115 bp fragment of the murine b$_{min}$-globin mRNA, upon cleavage at a cluster of mismatches. Radioactive bands corresponding to the specific protected fragments were scanned using a Phosphor Imager (Molecular Dynamics). The mRNA ratios were calculated on a per gene basis in MEL cells, which are pseudo-diploid for the endogenous murine globin genes (correction factor: 2). The mRNA ratio was also corrected for the number of uridine residues in each probe (44 for human d and 33 for murine $b_{maj}$; correction factor: 1.3). Global calculations were made as follows:

$$\frac{\text{Human } \delta}{\text{Murine } \beta\ maj} = \frac{[\text{Human } \delta\text{-globin band}] \times 2 \times 100}{2 \times [\text{Murine } \beta\ maj\text{-globin band}] \times 1.3}$$

Equivalents

Those skilled in the art will recognize, or be able to ascertain using no more than routine experimentation, many equivalents of the specific embodiments of the invention described herein. Such equivalents are intended to be encompassed by the following claims.

We claim:

1. An anti-sickling β-globin protein having structure of human β-globin and comprising the amino acid sequence shown in SEQ ID NO: 1, wherein at least one amino acid residue of SEQ ID NO: 1 has been substituted with an anti-sickling amino acid residue selected from the group consisting of: 9 Thr, 12 Asn, 22 Ala, 50 Ser, 80 Asp, 86 Ser, 87 Gln, 116 Arg, 117 Asn, 125 Gln and 126 Met, provided that said anti-sickling β-globin protein does not contain all of said anti-sickling residues, wherein said anti-sickling β-globin protein exhibits reduced sickling compared to wild-type β-globin protein when present in a hemoglobin tetramer along with at least one β 6 Val mutated β-globin protein.

2. The anti-sickling β-globin protein of claim 1 wherein said anti-sickling amino acid residue is selected from the group consisting of; 9 Thr, 12 Asn, 22 Ala, 50 Ser, 86 Ser, 87 Gln, 116 Arg, and 117 Asn, 125 Gln and 126 Met.

3. The anti-sickling β-globin protein of claim 1 having the amino acid sequence shown in SEQ ID NO:2.

4. The anti-sickling β-globin protein of claim 1 produced recombinantly in a host cell transformed with an expression vector comprising a nucleic acid encoding the protein.

5. The anti-sickling β-globin protein of claim 4 wherein said host cell is an erythroid cell.

6. The anti-sickling β-globin protein of claim 4 wherein said expression vector further comprises a promoter recognized by a DNA or an RNA polymerase.

7. The anti-sickling β-globin protein of claim 6 wherein said DNA or RNA polymerase is erythroid-specific and wherein said host cell is an erythroid cell.

8. The anti-sickling β-globin protein of claim 6 wherein said promoter is selected from the group consisting of the β-globin promoter and the HPFH promoter.

9. The anti-sickling β-globin protein of claim 6 wherein said expression vector further comprises an enhancer.

10. The anti-sickling β-globin protein of claim 9 wherein said enhancer is the DNAse I hypersensitive site 2 of the human β Locus Control Region and/or the second intron of the β-globin gene.

11. The anti-sickling β-globin protein of claim 4 further comprising a selectable marker.

* * * * *